United States Patent
Lee et al.

(10) Patent No.: US 10,599,944 B2
(45) Date of Patent: Mar. 24, 2020

(54) VISUAL FEEDBACK FOR INSPECTION ALGORITHMS AND FILTERS

(71) Applicant: KLA-Tencor Corporation, Milpitas, CA (US)

(72) Inventors: Hucheng Lee, Cupertino, CA (US); Junqing Huang, Fremont, CA (US); Lisheng Gao, Morgan Hill, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 228 days.

(21) Appl. No.: 13/685,808

(22) Filed: Nov. 27, 2012

(65) Prior Publication Data

US 2016/0210526 A1    Jul. 21, 2016

Related U.S. Application Data

(60) Provisional application No. 61/644,026, filed on May 8, 2012.

(51) Int. Cl.
*G06K 9/40*    (2006.01)
*G06F 3/048*    (2013.01)
(Continued)

(52) U.S. Cl.
CPC ............. *G06K 9/40* (2013.01); *G06F 3/048* (2013.01); *G06T 7/001* (2013.01);
(Continued)

(58) Field of Classification Search
CPC ..... G01B 11/30; G01B 11/303; G01B 11/306; G06K 9/40; G06F 3/048
(Continued)

(56) References Cited

U.S. PATENT DOCUMENTS 4,344,146 A * 8/1982 Davis et al. .................. 382/141
5,361,330 A * 11/1994 Fujisaki ................. G06K 15/00
                                                            345/418

(Continued)

FOREIGN PATENT DOCUMENTS

KR    10-2010-0014555 A    2/2010
KR    10-2010-0046240 A    5/2010

OTHER PUBLICATIONS

Anitha, S., and Radha, V., Contrast Stretching and Non Linear Median Filters for Fabric Inspection, International Journal of Computer Science and Information Technologies, vol. 2 (2) , pp. 836-839, available at https://pdfs.semanticscholar.org/cfc1/1ec9a4c80ecebd05bae8b9b4c3d0bd0c767d.pdf (2011).*

(Continued)

*Primary Examiner* — Sherief Badawi
*Assistant Examiner* — Conrad R Pack
(74) *Attorney, Agent, or Firm* — Suiter Swantz pc llo

(57) ABSTRACT

The disclosure is directed to providing visual feedback for inspection algorithms and difference filters used to process test and reference images from an inspection system. A user interface may be configured for displaying information and accepting user commands. A computing system communicatively coupled to the user interface may be configured to receive at least one set of test and reference images collected by the inspection system. The computing system may be further configured to provide at least one visual representation of the test and reference images via the user interface to show effects of an inspection algorithm and/or difference filter.

25 Claims, 8 Drawing Sheets

(51) Int. Cl.
*G06T 7/00* (2017.01)
*H01L 21/66* (2006.01)
*G01N 21/95* (2006.01)
*G01N 21/956* (2006.01)
*G01N 21/88* (2006.01)

(52) U.S. Cl.
CPC ..... *G01N 21/8851* (2013.01); *G01N 21/9501* (2013.01); *G01N 21/956* (2013.01); *G06T 2207/30148* (2013.01); *H01L 22/12* (2013.01); *H01L 22/20* (2013.01); *H01L 2924/0002* (2013.01)

(58) Field of Classification Search
USPC ........................................................ 715/810
See application file for complete search history.

(56) References Cited

U.S. PATENT DOCUMENTS

| | | | |
|---|---|---|---|
| 5,777,327 A * | 7/1998 | Mizuno | 250/310 |
| 5,861,952 A * | 1/1999 | Tsuji | G01N 21/94 356/484 |
| 6,072,900 A | 6/2000 | Chiu et al. | |
| 6,597,381 B1 * | 7/2003 | Eskridge et al. | 715/804 |
| 6,614,924 B1 | 9/2003 | Aghajan | |
| 6,898,333 B1 * | 5/2005 | Gopalakrishnan et al. | 382/289 |
| 7,440,607 B1 | 10/2008 | Lin et al. | |
| 7,508,973 B2 * | 3/2009 | Okabe et al. | 382/145 |
| 7,570,797 B1 | 8/2009 | Wang et al. | |
| 2001/0033683 A1 * | 10/2001 | Tanaka | G06T 7/001 382/149 |
| 2003/0025904 A1 * | 2/2003 | Sakai et al. | 356/237.2 |
| 2003/0161548 A1 * | 8/2003 | Vuylsteke | G06T 5/009 382/274 |
| 2003/0228049 A1 * | 12/2003 | Asai | 382/145 |
| 2004/0120601 A1 * | 6/2004 | Ruol | G06T 5/20 382/275 |
| 2004/0252879 A1 | 12/2004 | Tiemeyer et al. | |
| 2005/0213807 A1 * | 9/2005 | Wasserman | G06T 7/0004 382/152 |
| 2007/0081740 A1 * | 4/2007 | Ciudad | H04N 1/00286 382/276 |
| 2007/0177787 A1 * | 8/2007 | Maeda et al. | 382/141 |
| 2007/0194231 A1 * | 8/2007 | Nakahira et al. | 250/310 |
| 2008/0100942 A1 * | 5/2008 | Meier et al. | 360/31 |
| 2009/0009753 A1 | 1/2009 | Horai et al. | |
| 2009/0015698 A1 * | 1/2009 | Kim | H04N 5/357 348/294 |
| 2009/0034828 A1 * | 2/2009 | Ferro | G01N 29/0645 382/144 |
| 2010/0246948 A1 * | 9/2010 | Guarnieri | G06T 7/0002 382/167 |
| 2013/0336573 A1 * | 12/2013 | Dalla-Torre | G06T 7/001 382/145 |

OTHER PUBLICATIONS

Supplementary European Search Report for Application No. EP 13788048 dated Feb. 18, 2016, 10 pages.
Wikipedia, The Free Encyclopedia, Signal-to-noise ratio, Printed online at: https://en.wikipedia.org/wiki/Signal-to-noise_ratio, Jul. 30, 2017, 8 pages.
Image Processing Learning Resources, Pixel Subtraction, Printed online at: http://homepages.inf.ed.ac.uk/rbf/HIPR2/pixsub.htm, ©2003 R. Fisher, S. Perkins, A. Walker and E. Wolfart, 5 pages.

* cited by examiner

VISUAL FEEDBACK FOR INSPECTION ALGORITHMS AND FILTERS

PRIORITY

The present application claims priority to U.S. Provisional Application Ser. No. 61/644,026, entitled DIFF FILTER AND GENERALIZED MDAT SETUP UI DESIGN, by Hucheng Lee et al., filed May 8, 2012, which is currently co-pending, or is an application of which a currently co-pending application is entitled to the benefit of the filing date.

TECHNICAL FIELD

The present disclosure generally relates to the field of inspection systems and more particularly to providing visual feedback for inspection algorithms and/or filters used to process test and reference images collected by an inspection system.

BACKGROUND

Semi-conductor fabrication is being driven towards smaller scale and higher complexity production. To implement tighter specifications, inspection systems may be used at various stages before, during, and/or after the fabrication process. At any of the foregoing stages, one or more defects of a tested sample can be detected and characterized utilizing an inspection system, such as a brightfield inspection system, darkfield inspection system, e-Beam inspection system, and the like.

Inspection systems may be configured to collect test and reference images of the sample, which are then analyzed to detect sample defects. The test and reference images may be filtered or processed utilizing a selected inspection algorithm to improve defect detection and separation. However, difference filters and inspection algorithms can be difficult to setup and evaluate because it is not possible to directly observe effects of a selected filter or inspection algorithm on the processed test and reference images. Application engineers and customers tend to avoid utilizing difference filters or modifying inspection algorithm settings due to the foregoing difficulties in ascertaining appropriate settings.

SUMMARY

The present disclosure is directed to providing visual feedback regarding effects of a selected difference filter or inspection algorithm on at least one set of test and reference images (hereinafter "sample images") collected by an inspection system. The visual feedback may enable selection of difference filter and/or inspection algorithm settings for improved defect detection and separation.

In one aspect, the present disclosure is directed to a system for processing at least one set of sample images. The system may include a user interface configured for displaying information and accepting user commands and a computing system communicatively coupled to the user interface. The computing system may be configured to receive at least one set of sample images. The computing system may be further configured to process the sample images utilizing a selected inspection algorithm and/or a selected difference filter. The computing system may be further configured to provide at least one visual representation of the sample images via the user interface. The visual representation may include at least one of: a signed difference image having values at pixels of the signed difference image to identify polarity of at least one defect of the sample, a side-by-side view of an original difference image and a filtered difference image, a cursor configured for selecting one or more pixels associated with at least one defect of the sample, and a binary scatter plot generated utilizing an inspection algorithm.

In another aspect, the present disclosure is directed to a system for processing at least one set of sample images received from an inspection system. The system may include an inspection system, a user interface, and a computing system. The user interface may be configured for displaying information and accepting user commands. The inspection system may be configured to collect at least one set of sample images. The computing system may be communicatively coupled to the user interface and to the inspection system. The computing system may be configured to receive the sample images from the inspection system. The computing system may be further configured to process the sample images utilizing a selected inspection algorithm and/or a selected difference filter. The computing system may be further configured to provide at least one visual representation of the sample images via the user interface. The visual representation may include at least one of: a signed difference image having values at pixels of the signed difference image to identify polarity of at least one defect of the sample, a side-by-side view of an original difference image and a filtered difference image, a cursor configured for selecting one or more pixels associated with at least one defect of the sample, and a binary scatter plot generated utilizing an inspection algorithm.

In another aspect, the present disclosure is directed to a method of processing at least one set of sample images, including the steps of: receiving at least one set of sample images collected utilizing an inspection system; processing the sample images utilizing a selected inspection algorithm and/or a selected difference filter; and providing at least one visual representation of the sample images via a user interface. The visual representation may include at least one of: a signed difference image having values at pixels of the signed difference image to identify polarity of at least one defect of the sample, a side-by-side view of an original difference image and a filtered difference image, a cursor configured for selecting one or more pixels associated with at least one defect of the sample, and a binary scatter plot generated utilizing an inspection algorithm.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

FIGS. 1 through 4 generally illustrate a system and method for providing visual feedback regarding effects of a selected inspection algorithm and/or difference filter on at least one set of test and reference images (hereinafter "sample images") of at least one sample. The sample images may be collected by an inspection system such as, but not limited to, a brightfield, darkfield, or e-Beam inspection system. Visual representations of the sample images may be observed and various filter, algorithm, and/or view options may be manipulated via a user interface to improve ability to detect and/or separate defects. Inspection algorithm settings and/or difference filter templates may be selected based upon the observed visual representations. The embodiments that follow illustrate the foregoing principles in greater detail.

As used throughout the present disclosure, the term "sample" generally refers to a patterned or unpatterned wafer. In some embodiments, however, a sample may include at least a portion of a storage medium such as, but not limited to, a hard disk drive (HDD). In some embodiments, a sample may include a substrate formed of a semiconductor or non-semiconductor material such as, but not limited to, monocrystalline silicon, gallium arsenide, and indium phosphide. In some embodiments, the sample may further include one or more "layers" formed on the substrate such as, but not limited to, a resist, a dielectric material, a conductive material, or a semiconductive material. Many different types of substrates, sample layers, and storage media are known in the art. Accordingly, the foregoing illustrations of the term "sample" should not be construed as limiting the disclosure in any way.

Figure 1:
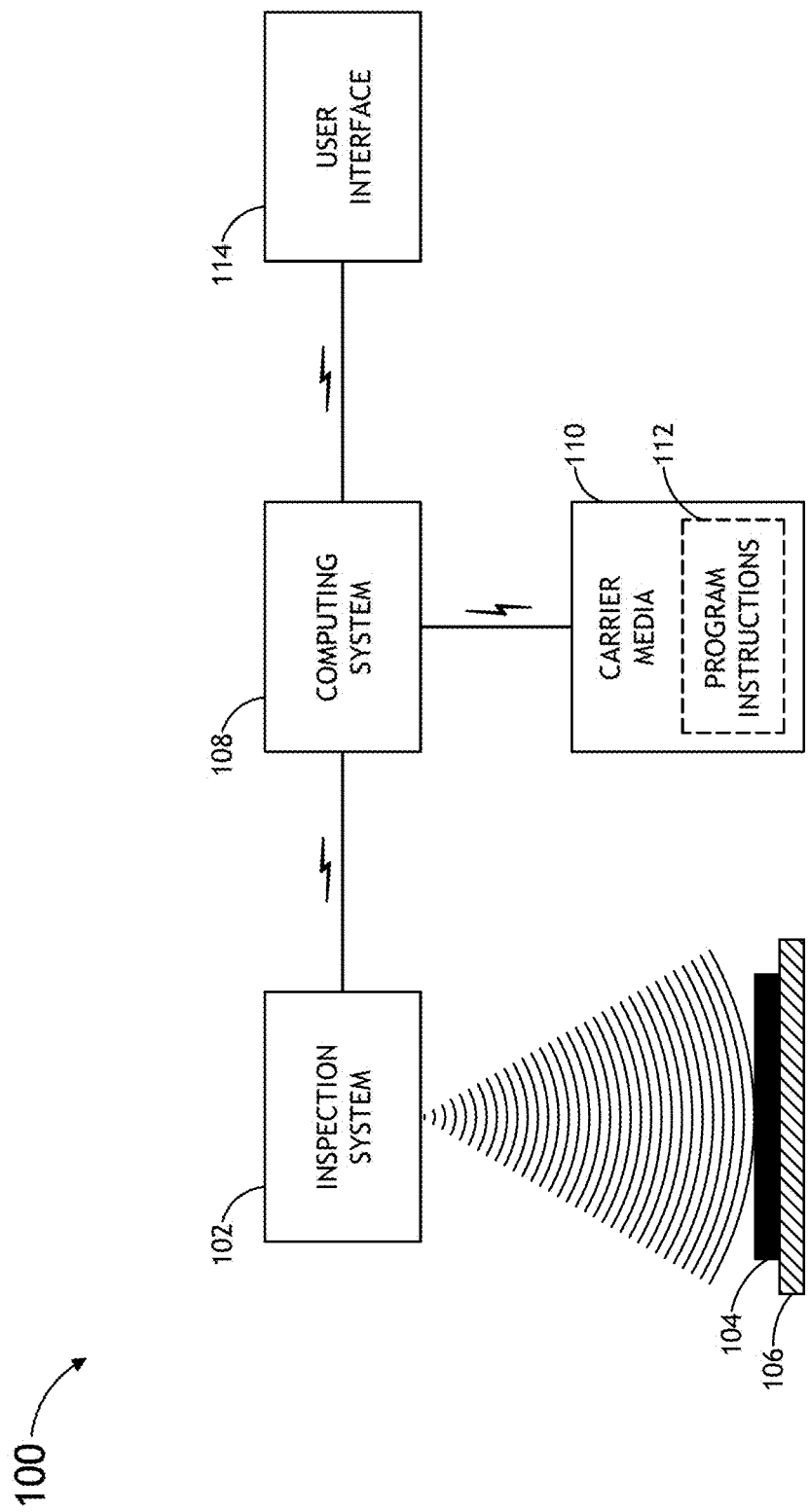
FIG. 1 is a block diagram illustrating a system for processing at least one set of sample images, in accordance with an embodiment of this disclosure.

FIG. 1 illustrates an embodiment of a system 100 for processing sample images by providing visual feedback regarding effects of a selected inspection algorithm and/or difference filter. An inspection system 102 may be configured to collect at least one set of sample images of at least one sample 104 disposed upon a sample stage 106. A computing system 108 may be configured to receive the sample images collected by the inspection system 102. The computing system 108 may include any combination of software, hardware, and/or firmware configured to carry out one or more functions or steps described herein. In an embodiment, the computing system 108 may include one or more processors configured to execute program instructions 112 from carrier media 110.

The computing system 108 may be coupled to a user interface 114 configured for displaying information and/or accepting user commands. The user interface 114 may include at least one display unit such as, but not limited to, a LCD, LED, plasma, CRT, or projection display configured for providing a graphical user interface and visual representations of the sample images before or after processing by a selected inspection algorithm and/or difference filter. The user interface 114 may further include an input device such as, but not limited to, a keyboard, mouse, buttons, trackball, dial, touchpad, touchscreen, or microphone configured for accepting user commands, requests, selections, and the like.

In one embodiment, the computing system 108 may be communicatively coupled to the inspection system 102. The computing system 108 may be configured to receive sample images transmitted over a wired or wireless data connection (e.g. direct communication link, ad-hoc communication network, LAN, WAN) from the inspection system 102. In a further embodiment, the inspection system 102 may include the computing system 108 and the user interface 114. Functions of the computing system 108 and user interface 114 described herein may be integrated into a computing system 108 and user interface 114 of the inspection system 102. In another embodiment, the computing system 108 and user interface 114 may be disconnected from the inspection system 102. Sample images may be downloaded from the inspection system 102 to a transportable carrier media such as, but not limited to, a flash drive or memory card. The computing system 108 may be configured to receive the sample images from the transportable carrier media for processing and analysis. Any description of the computing system 108, user interface 114, and/or inspection system 102 shall apply to any of the foregoing arrangements, unless otherwise noted.

The computing system 108 may be configured to filter the sample images utilizing a selected difference filter. In an embodiment, the selected difference filter may be chosen from a plurality of difference filter templates. The difference filter templates may include pre-defined filters such as, but not limited to, highpass, lowpass, hybrid, narrowband, vertical-direction, horizontal-direction, and other selected direction filters. In some embodiments, a filter template, such as a selected direction filter, may allow improved detection of certain defects of the sample 104, such as scratches on a wafer. The difference filter templates may further include customized or customizable filters having selectively adjustable parameters. The computing system 108 may be further configured to apply an inspection algorithm such as, but not limited to, a multiple die adaptive-thresholding (MDAT) or generalized MDAT algorithm to process filtered and/or unfiltered difference images for defect detection. Embodiments of inspection algorithms are further described in U.S. Pat. No. 7,440,607, incorporated herein by reference. In some embodiments, the computing system 108 may be further configured to filter the sample images using an energy filter, IMX filter, or fuzzy difference filter.

Figure 2A:
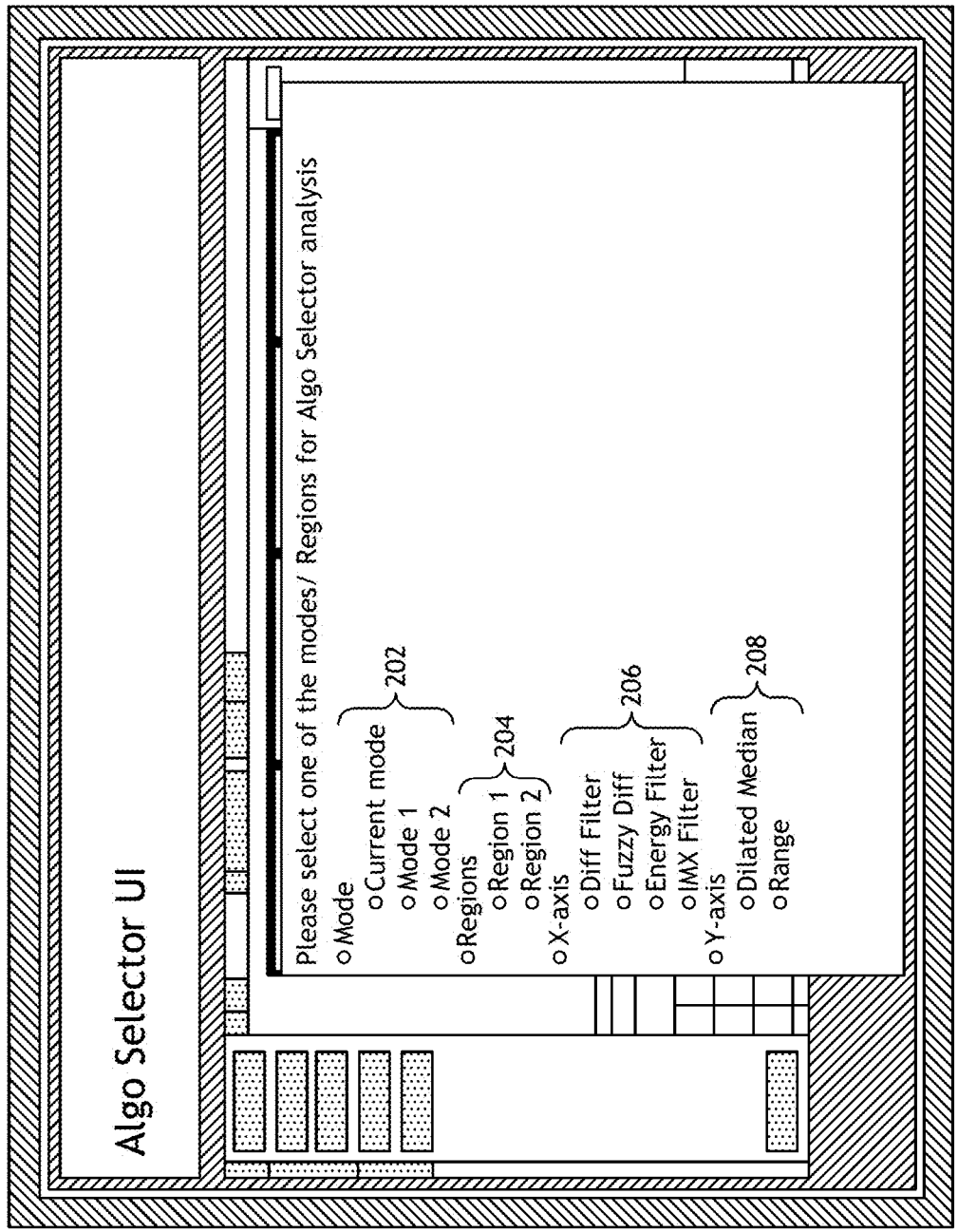
FIG. 2A is a conceptual illustration of a graphical user interface, in accordance with an embodiment of this disclosure.
Figure 2B:
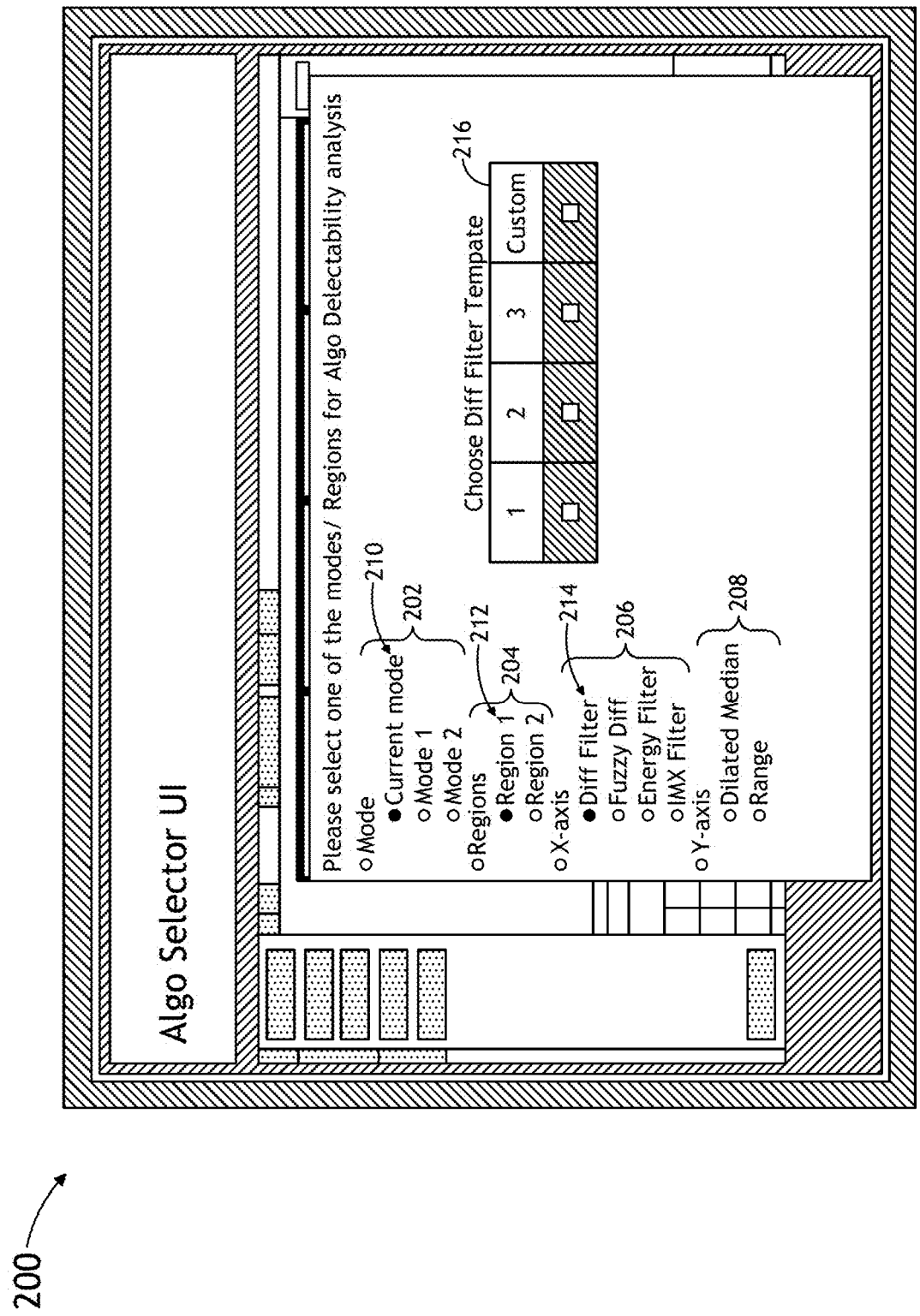
FIG. 2B is a conceptual illustration of a graphical user interface, wherein a plurality of difference filter templates is displayed, in accordance with an embodiment of this disclosure.

As illustrated in FIGS. 2A and 2B, the computing system 108 may be further configured to provide a graphical user interface (GUI) 200 including a plurality of user options through a display unit of the user interface 114. The GUI 200 may include a plurality of modes 202, regions 204, X-axis parameters 206, and/or Y-axis parameters 208 available for user selection. As illustrated in FIG. 2B, the GUI 200 may further include at least one indication of a selected mode 210, region 212, X-axis parameter 214, and/or Y-axis parameter. The GUI 200 may further include a plurality of filter templates 216 available for selection. For example, when the selected X-axis parameter 214 is a difference filter, the GUI 200 may provide the plurality of difference filter templates 216 available for selection. The computing system 108 may be further configured to receive user selections via the user interface 114 to allow user interaction with the GUI 200. In another embodiment, the GUI 200 may be integrated within a GUI of the inspection system 102. For example, an optics selector of the inspection system may include the GUI 200.

FIGS. 3A through 3D illustrate visual representations 300 of the sample images that may be provided via the user interface 114 for visual feedback regarding effects of the selected inspection algorithm and/or difference filter. In some embodiments, at least one difference image may be extracted from the sample images. The difference image may be determined based on a comparison of the test and reference images of the sample 104. In an embodiment, illustrated in FIG. 3A, the visual representation 300 may include at least one signed difference image 302 with a positive or negative value at each pixel to identify polarity of at least one defect. For example, the signed difference image 302A or 302B may include negative values at pixels of a defect having dark polarity or positive values at pixels of a defect having bright polarity, respectively.

The visual representation 300 may further include a cursor 304 controlled via an input device of the user interface 114. The cursor 304 may be configured for selecting one or more pixels associated with at least one defect of the sample 104. The pixels may delineate a region of interest for analysis, such as a selected defect or selected portion of a defect. The user can mark multiple defective pixels in the region of interest from which signal value S is calculated. Current signal box can be used to exclude pixels in the box from being considered as noise. In an embodiment, locations of marked defect pixels for one inspection mode may be applied to other inspection modes. However, corrections may be accepted via the user interface 114 for potential image shifts and/or stage accuracy (e.g., the user can correct the defect pixels for other inspection modes).

In a further embodiment, signal-to-noise ratio (SNR) and/or absolute difference (|S-N|) of the defect may be determined utilizing information about defect polarity. For example, noise having the same polarity as the defect may be used to calculate SNR or |S-N|, within a default or custom range of a selected reference median gray level or reference roughness or of corresponding segmentation breaks for generalized MDAT, centered around the defect. Noise (N) used to calculate SNR or |S-N| may be of the same sign as defect signal S, within a range (e.g., noise band, set default range, but user should be able to adjust) of reference median gray level, or reference roughness specified by user, or the corresponding segmentation breaks for generalized MDAT, centered around the defect. Furthermore, noise having opposite polarity may be excluded from SNR or |S-N| determination.

Figure 3A:
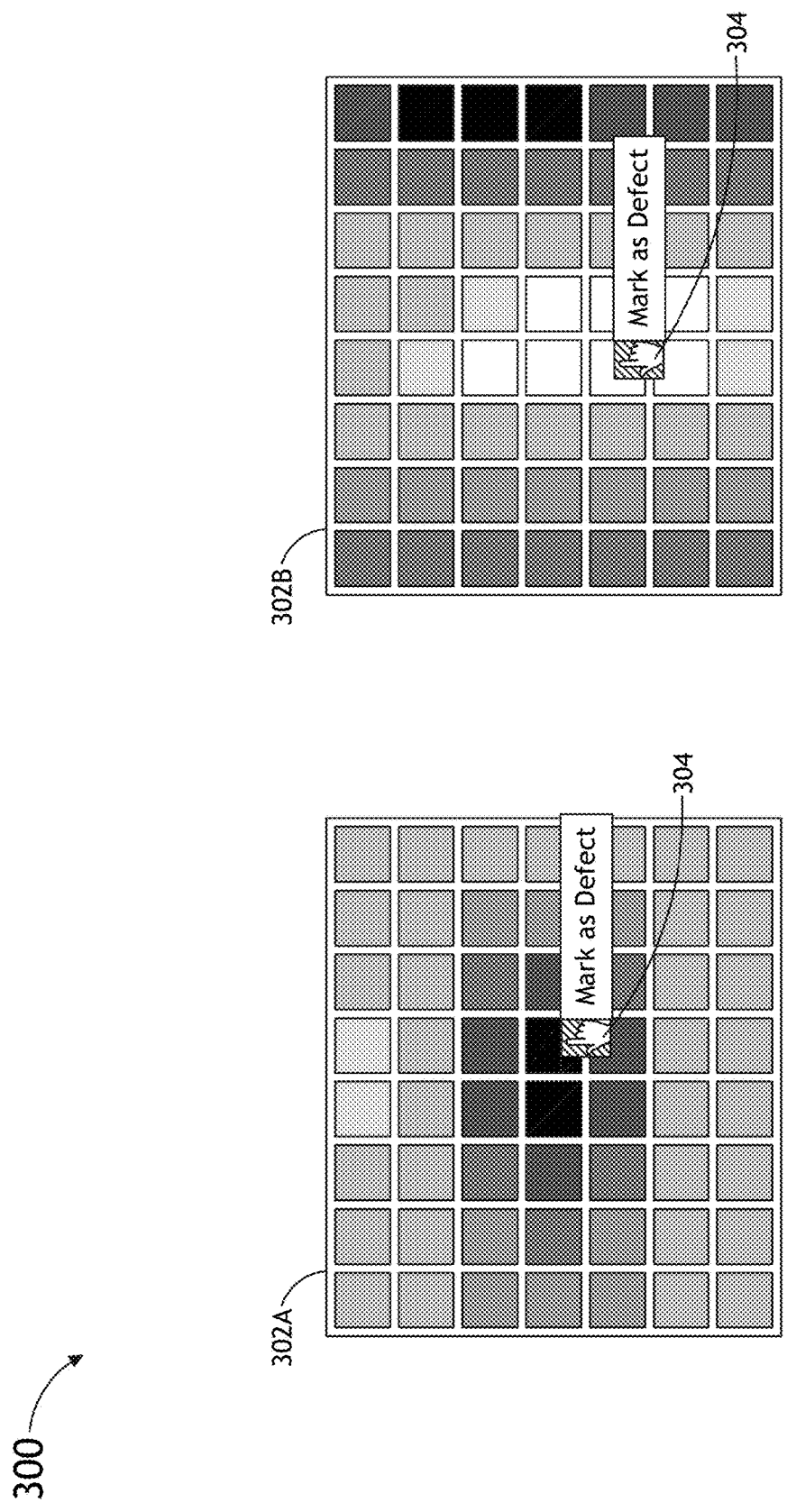
FIG. 3A is a conceptual illustration of a visual representation of at least one set of sample images, wherein the visual representation includes a signed difference image, in accordance with an embodiment of this disclosure.
Figure 3B:
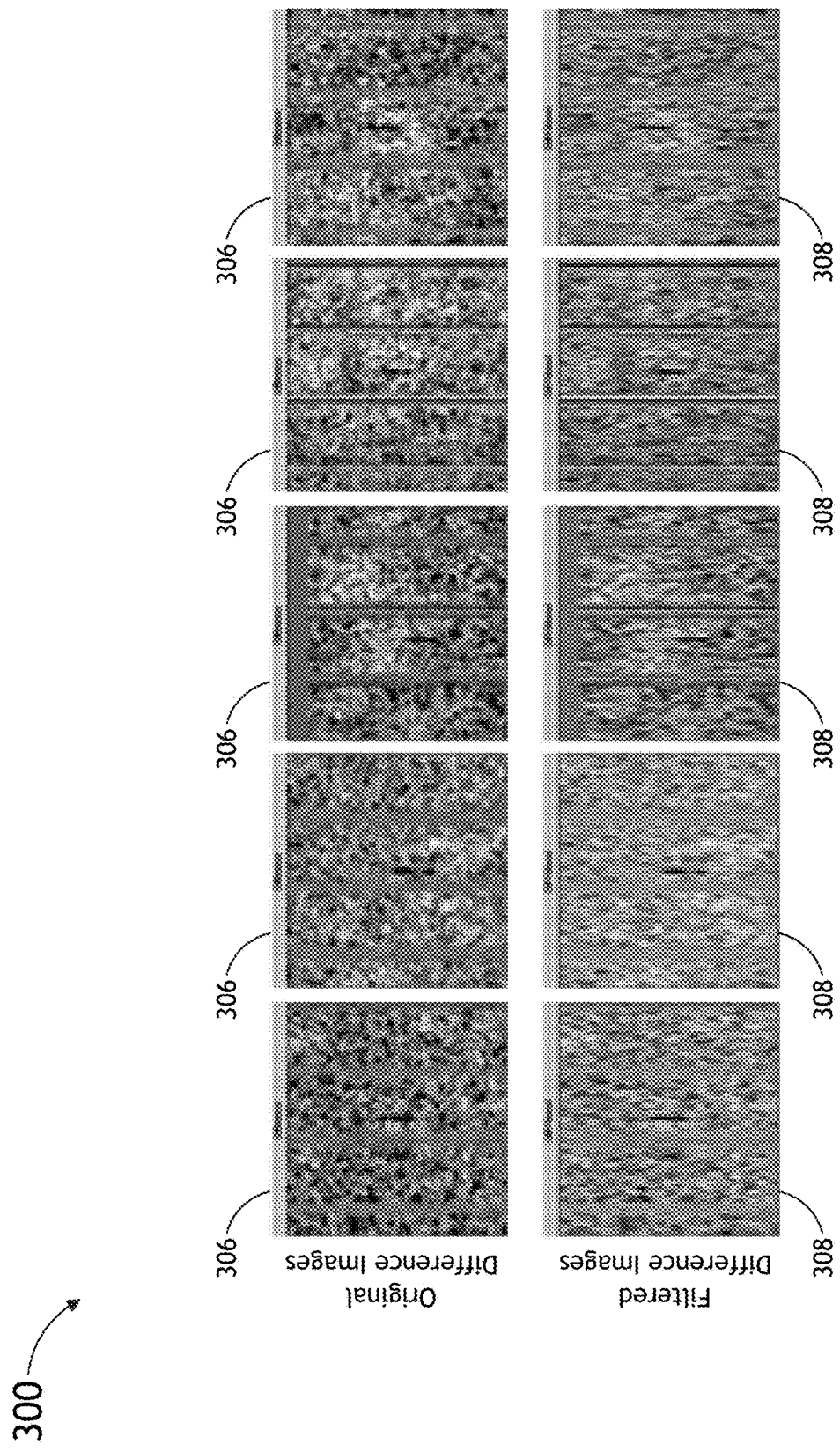
FIG. 3B is a conceptual illustration of a visual representation of at least one set of sample images, wherein the visual representation includes at least one original difference image and at least one filtered difference image, in accordance with an embodiment of this disclosure.
Figure 3C:
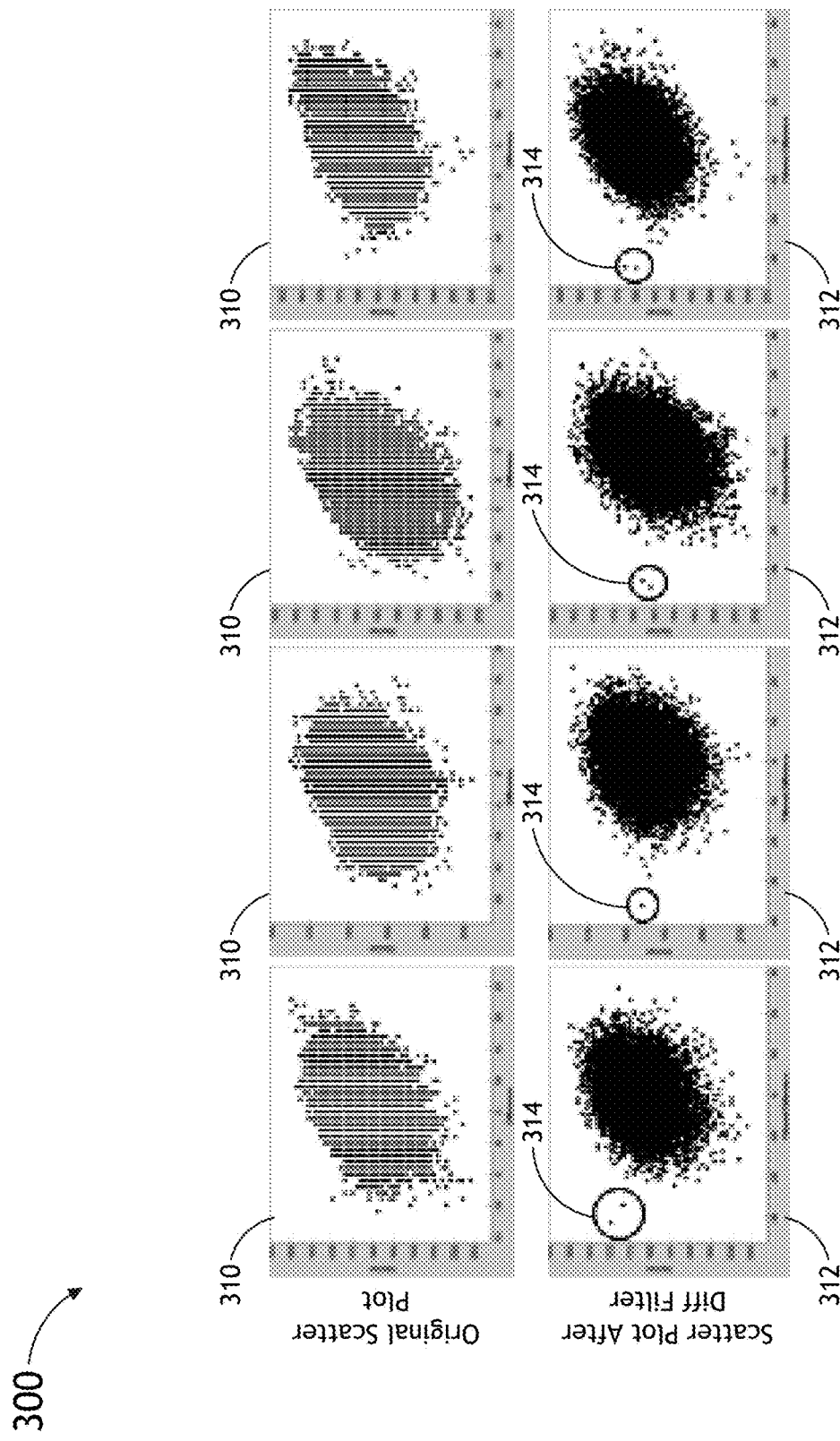
FIG. 3C is a conceptual illustration of a visual representation of at least one set of sample images, wherein the visual representation includes at least one binary scatter plot generated utilizing a selected inspection algorithm, in accordance with an embodiment of this disclosure.
Figure 3D:
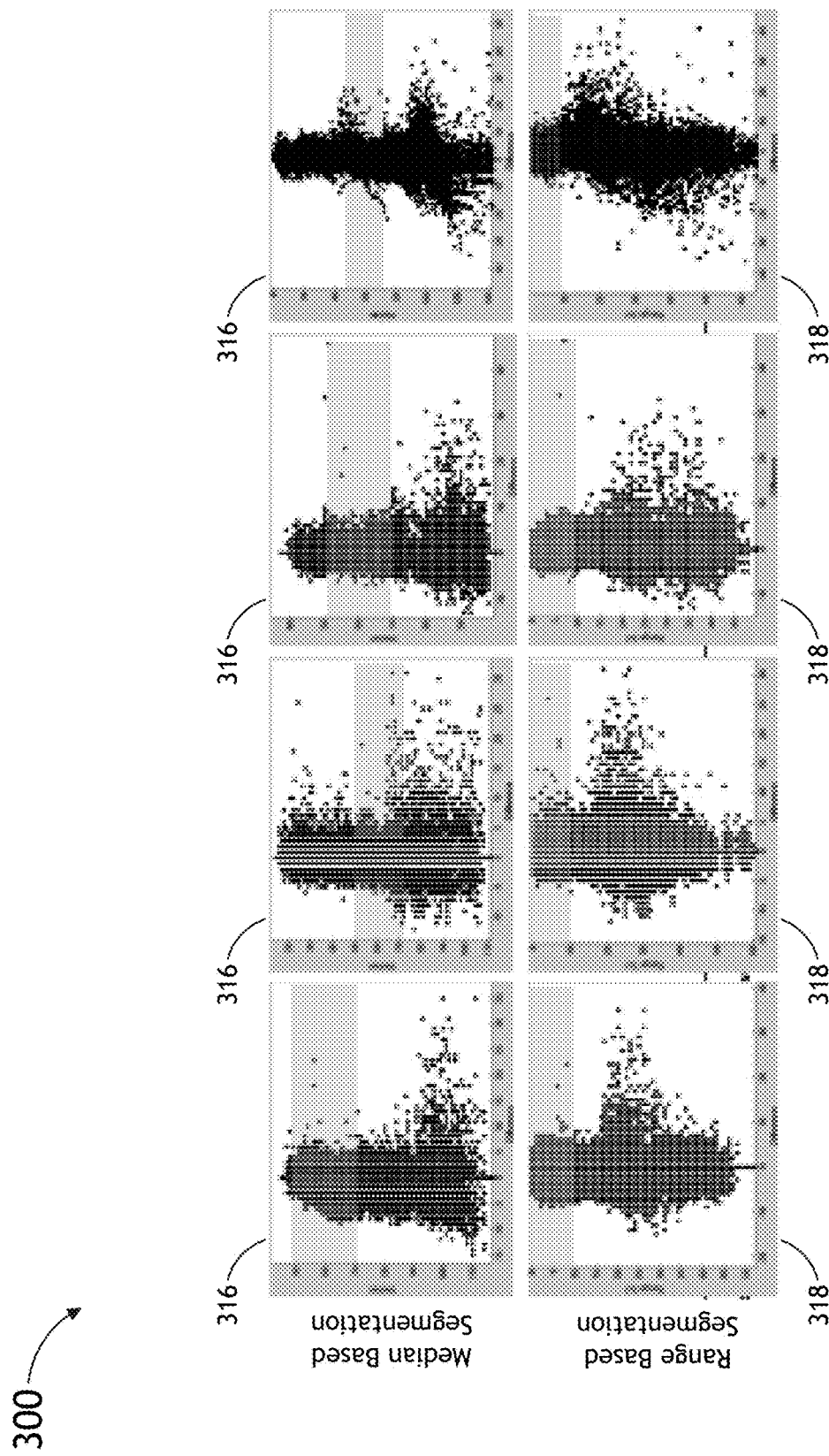
FIG. 3D is a conceptual illustration of a visual representation of at least one set of sample images, wherein the visual representation includes at least one binary scatter plot segmented in response to a selected y-axis parameter, in accordance with an embodiment of this disclosure.

In another embodiment, illustrated in FIG. 3B, the visual representation 300 may include a side-by-side view of at least one original difference image 306 and at least one filtered difference image 308. The effects of the difference filter may be ascertained by visual comparison of the unfiltered and filtered images 306, 308. In another embodiment, illustrated in FIG. 3C, the visual representation 300 may include at least one binary scatter plot 310, 312 generated utilizing the selected inspection algorithm.

In an embodiment, the binary scatter plot 310, 312 may include a plurality of markers representing pixels of a filtered or unfiltered difference image. For example, each marker may correspond to one pixel or a selected number of pixels of the difference image. The X-axis may correspond to the selected difference filter or any other selected filter. In one embodiment, the visual representation 300 may further include a side-by-side view of at least one binary scatter plot 310 of the unfiltered difference image and at least one binary scatter plot 312 of the filtered difference image. The side-by-side view may allow visual comparison to ascertain a change in ability to detect defects 314 resulting from filtering the difference image utilizing the selected difference filter.

In an embodiment, the visual representation 300 may further include at least one binary scatter plot 316, 318 segmented in response to a selected Y-axis parameter. The selected Y-axis parameter may include, but is not limited to, median, dilated median, or range based segmentation. In one embodiment, the visual representation 300 may further include a side-by-side view of at least one binary scatter plot 316 having a first segmentation (e.g. median based) and at least one binary scatter plot 318 having a second segmentation (e.g. range based) to allow visual comparison of effects resulting from changing the inspection algorithm plotting options.

In another embodiment, the visual representation 300 may include at least one density scatter plot, wherein the number of pixels for each location of the difference image are represented using a plurality of colors. A first color (e.g. black) may represent the absence of pixels. A second color (e.g. green) may represent high pixel density. A third color (e.g. red) may represent pixels of the defect. In an embodiment, the visual representation 300 may further include a side-by-side view of at least one density scatter plot of an unfiltered difference image and at least one density scatter plot of a filtered difference image to allow visual comparison to ascertain effects of the difference filter.

In another embodiment, the visual representation 300 may further include a table with a plurality of signal, noise, SNR, |S-N| and/or MDAT offsets for numerical comparison of various filter and/or algorithm settings. The table may include a sorted chart of signal, noise, SNR, and/or |S-N| information allowing comparison to ascertain effects of the selected inspection algorithm and/or difference filter.

In an embodiment, the computing system 108 may be further configured to store at least one set of selected settings for the inspection algorithm and/or difference filter. The computing system 108 may be configured to retrieve the stored settings for future inspections or for processing sample images at any selected time. In an embodiment, the stored settings may be an optimal or user selected configuration based upon one or more of the visual representations 300 provided via the user interface 114.

Figure 4:
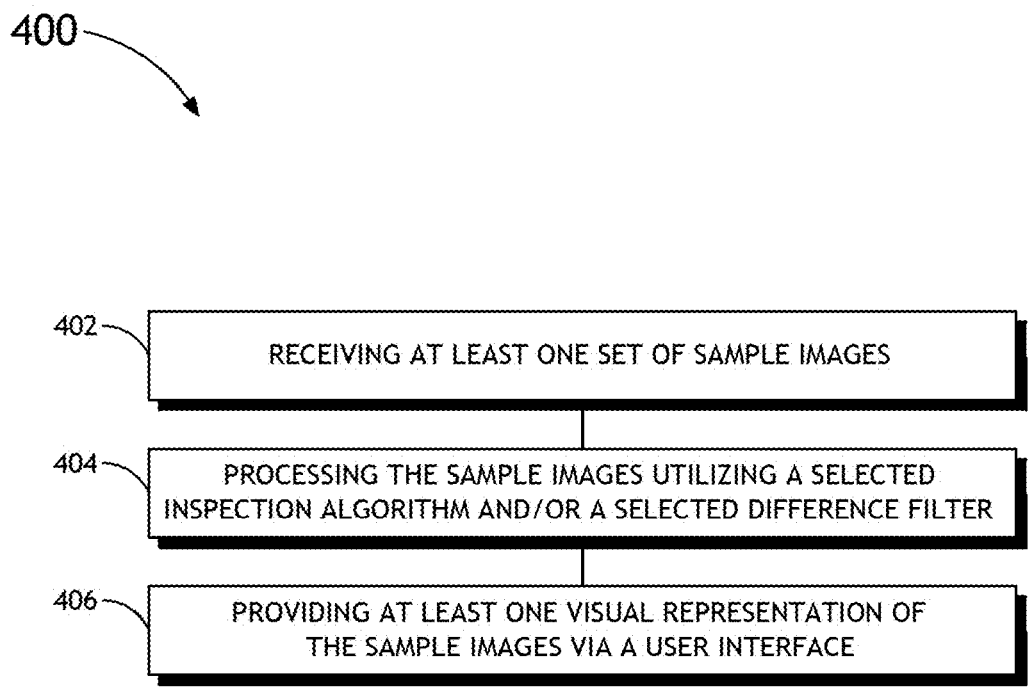
FIG. 4 is a flow diagram illustrating a method of processing at least one set of sample images, in accordance with an embodiment of this disclosure.

FIG. 4 illustrates a method 400 of processing at least one set of sample images by providing visual feedback regarding effects of a selected inspection algorithm and/or difference filter. It is noted herein that embodiments of system 100 are manifestations of method 400. However, it is contemplated that one or more steps of method 400 may be accomplished via other means known to the art. Accordingly, method 400 should be construed as broadly encompassing any means for carrying out the steps described herein.

At step 402, at least one set of sample images of at least one sample 104 are received from an inspection system 102. At step 404, the sample images are processed utilizing a selected inspection algorithm and/or difference filter. In an embodiment, a plurality of inspection algorithm options and/or difference filter templates may be provided via a display unit of the user interface 114 for selection. One or more user command may be received via an input device of the user interface 114 to designate selected inspection algorithm settings and/or a difference filter chosen from the plurality of filter templates. At step 406, at least one visual representation 300 of the sample images is provided via the user interface 114 to convey effects of the selected inspection algorithm and/or difference filter. Difference filter and/or inspection algorithm settings may be adjusted based on the visual feedback. Furthermore, the selected inspection algorithm and/or difference filter settings may be stored for use at any selected time.

It is contemplated that each of the embodiments of the method described above may include any other step(s) of any other method(s) described herein. In addition, each of the embodiments of the method described above may be performed by any of the systems described herein.

It should be recognized that the various steps described throughout the present disclosure may be carried out by a single computing system or by multiple computing systems. Moreover, different subsystems of the system may include a computing system suitable for carrying out at least a portion of the steps described above. Therefore, the above description should not be interpreted as a limitation on the present invention but merely an illustration. Further, the one or more computing systems may be configured to perform any other step(s) of any of the method embodiments described herein.

The computing system may include, but is not limited to, a personal computing system, mainframe computing system, workstation, image computer, parallel processor, or any other device known in the art. In general, the term "computing system" may be broadly defined to encompass any device having one or more processors, which execute instructions from a memory medium.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. Program instructions implementing methods such as those described herein may be transmitted over or stored on carrier medium. The carrier medium may be a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. A system for processing at least one set of sample images, comprising:
a user interface configured for displaying information and accepting user commands; and
a computing system including one or more processors communicatively coupled to the user interface, the one or more processors configured to:
receive at least one original difference image of a sample;
receive a user selection, from the user interface, of a difference filter for application on at least one of the at least one original difference image of the sample;
process the at least one original difference image with the difference filter to form at least one filtered difference image;
provide a side-by-side view of a visual representation of the at least one original difference image and the filtered difference image via the user interface, the visual representation including a difference image having values at pixels of the difference image to identify at least one defect in the at least one filtered image;
adjust one or more parameters of the difference filter;
receive a user selection, from the user interface, of a location of one or more pixels associated with at least one defect;
provide the location of one or more pixels associated with at least one defect to an additional inspection mode;
store one or more parameters of the difference filter for use at a selected time;
receive a user selection, from the user interface, of a selected reference median gray level range, wherein the selected reference median gray level range is displayed centered around at least one defect in a signed difference image of the sample; and
determine a signal-to-noise ratio (SNR) and an absolute difference of signal to noise (|S-N|) for at least one defect of the signed difference image of the sample based on the user selection of the location of one or more pixels associated with at least one defect, wherein the noise used to calculate SNR and |S-N| is within the selected reference median gray level range and is of a same sign as a signal of the one or more pixels associated with at least one defect, and wherein the signal-to-noise ratio (SNR) and the absolute difference of signal to noise (|S-N|) are displayed to the user via the user interface.

2. The system of claim 1, wherein the difference filter includes at least one of:
a highpass filter, a lowpass filter, a narrow band filter, a vertical-direction filter, a horizontal-direction filter, a selected direction filter, or a customizable filter.

3. The system of claim 1, wherein the difference image has values at pixels of the difference image to identify polarity of at least one defect of the at least one sample, wherein positive and negative values differentiate between bright polarity and dark polarity.

4. The system of claim 1, wherein the visual representation includes a binary scatter plot including a plurality of markers representing a plurality of pixels of the difference image, wherein each pixel is represented by a corresponding marker.

5. The system of claim 1, wherein the visual representation includes a binary scatter plot segmented in response to a selected y-axis parameter.

6. The system of claim 5, wherein the one or more processors of the computing system are further configured to:
provide a plurality of y-axis parameters via the user interface; and
receive a user command designating a selected y-axis parameter, chosen from the plurality of y-axis parameters.

7. The system of claim 6, wherein the plurality of y-axis parameters includes at least one of:
median, dilated median, or range.

8. A system for processing at least one set of sample images, comprising:
an inspection system configured to collect at least one original difference image;
a user interface configured for displaying information and accepting user commands; and
a computing system including one or more processors communicatively coupled to the user interface and the inspection system, the one or more processors configured to:
receive the at least one original difference image of a sample;
receive a user selection, from the user interface, of a difference filter for application on the at least one original difference image of the sample;
process the at least one original difference image with the difference filter to form at least one filtered difference image;
provide a side-by-side view of a visual representation of the at least one original difference image and a filtered difference image via the user interface, the visual representation including a difference image having values at pixels of the difference image to identify at least one defect in the filtered difference image;
adjust one or more parameters of the difference filter;
receive a user selection, from the user interface, of one or more pixels associated with at least one defect;
provide the location of one or more pixels associated with at least one defect to an additional inspection mode;
store one or more parameters of the difference filter for use at a selected time;
receive a user selection, from the user interface, of a selected reference median gray level range, wherein the selected reference median gray level range is displayed centered around at least one defect in a signed difference image of the sample; and
determine a signal-to-noise ratio (SNR) and an absolute difference of signal to noise (|S-N|) for at least one defect of the at least one sample based on the user selection of the location of one or more pixels associated with at least one defect, wherein the noise (N) used to calculate SNR and |S-N| is within the selected reference median gray level range and is of a same sign as a signal of the one or more pixels associated with at least one defect, and wherein the signal-to-noise ratio (SNR) and the absolute difference of signal to noise (|S-N|) are displayed to the user via the user interface.

9. The system of claim 8, wherein the difference filter includes at least one of:
a highpass filter, a lowpass filter, a narrow band filter, a vertical-direction filter, a horizontal-direction filter, a selected direction filter, or a customizable filter.

10. The system of claim 8, wherein the difference image has values at pixels of the difference image to identify polarity of at least one defect of the at least one sample, wherein positive and negative values differentiate between bright polarity and dark polarity.

11. The system of claim 8, wherein the visual representation includes a binary scatter plot including a plurality of markers representing a plurality of pixels of the difference image, wherein each pixel is represented by a corresponding marker.

12. The system of claim 8, wherein the visual representation includes a binary scatter plot segmented in response to a selected y-axis parameter.

13. The system of claim 12, wherein the one or more processors of the computing system is further configured to:
provide a plurality of y-axis parameters via the user interface; and
receive a user command designating a selected y-axis parameter, chosen from the plurality of y-axis parameters.

14. The system of claim 13, wherein the plurality of y-axis parameters includes at least one of:
median, dilated median, or range.

15. The system of claim 8, wherein the inspection system includes at least one of:
a brightfield inspection system, a darkfield inspection system, or an e-beam inspection system.

16. A method of processing at least one set of sample images, comprising:
receiving at least one original difference image collected utilizing an inspection system;
receiving a user selection, from a user interface, of a difference filter for application on the at least one original difference image of a sample;
processing the at least one original difference image with the difference filter to form at least one filtered difference image;
providing a side-by-side view of a visual representation of the at least one original difference image and a filtered difference image via the user interface, the visual representation including a difference image having values at pixels of the difference image to identify at least one defect in the at least one filtered difference image;
adjusting one or more parameters of the difference filter;
receiving a user selection, from the user interface, of one or more pixels associated with at least one defect;
providing the location of one or more pixels associated with at least one defect to an additional inspection mode;
storing one or more parameters of the difference filter for use at a selected time;
receiving a user selection, from the user interface, of a selected reference median gray level range, wherein the selected reference median gray level range is displayed centered around at least one defect in a signed difference image of the sample;

determining a signal-to-noise ratio (SNR) and an absolute difference of signal to noise (|S-N|) for at least one defect of the at least one sample based on the user selection of the location of one or more pixels associated with at least one defect, wherein the noise used to calculate SNR and |S-N| is within the selected reference median gray level range and is of a same sign as a signal of the one or more pixels associated with at least one defect; and displaying the signal-to-noise ratio (SNR) and the absolute difference of signal to noise (|S-N|) via the user interface.

17. The method of claim 16, wherein the difference filter includes at least one of:
a highpass filter, a lowpass filter, a narrow band filter, a vertical-direction filter, a horizontal-direction filter, a selected direction filter, or a customizable filter.

18. The method of claim 16, wherein the difference image has values at pixels of the difference image to identify polarity of at least one defect of the at least one sample, wherein positive and negative values differentiate between bright polarity and dark polarity.

19. The method of claim 16, wherein the visual representation includes a binary scatter plot including a plurality of markers representing a plurality of pixels of the difference image, wherein each pixel is represented by a corresponding marker.

20. The method of claim 16, wherein the visual representation includes a binary scatter plot segmented in response to a selected y-axis parameter.

21. The method of claim 20, further comprising:
providing a plurality of y-axis parameters via the user interface; and
receiving a user command designating a selected y-axis parameter, chosen from the plurality of y-axis parameters.

22. The method of claim 21, wherein the plurality of y-axis parameters includes at least one of:
median, dilated median, or range.

23. The method of claim 16, wherein the inspection system includes at least one of:
a brightfield inspection system, a darkfield inspection system, or an e-beam inspection system.

24. The system of claim 1, wherein the one or more processors of the computing system are further configured to:
receive a user selection, from the user interface, of one or more pixels of the difference image, wherein the difference image is associated with the at least one defect of the at least one sample, wherein the one or more selected pixels of the difference image delineate a region of interest for analysis of the difference image by the one or more processors.

25. The system of claim 1, wherein providing the location of the one or more pixels associated with at least one defect to an additional inspection mode comprises:
receiving a user selection, from the user interface, a correction of one or more pixels associated with the at least one defect; and
providing the correction of one or more pixels to the additional inspection mode, wherein the correction of one or more pixels is provided to correct at least one of an image shift or stage accuracy.

* * * * *